US010018543B1

(12) United States Patent
Wiederin et al.

(10) Patent No.: US 10,018,543 B1
(45) Date of Patent: Jul. 10, 2018

(54) PURIFYING AN ELEMENT FROM A SAMPLE MATRIX FOR ISOTOPIC ANALYSIS

(71) Applicant: Elemental Scientific, Inc., Omaha, NE (US)

(72) Inventors: Daniel R. Wiederin, Omaha, NE (US); Paul Field, Papillion, NE (US)

(73) Assignee: ELEMENTAL SCIENTIFIC, INC., Omaha, NE (US)

( * ) Notice: Subject to any disclaimer, the term of this patent is extended or adjusted under 35 U.S.C. 154(b) by 419 days.

(21) Appl. No.: 14/297,590

(22) Filed: Jun. 5, 2014

Related U.S. Application Data (60) Provisional application No. 61/831,536, filed on Jun. 5, 2013.

(51) Int. Cl.
    *G01N 1/34* (2006.01)
    *G01N 30/02* (2006.01)
    *G01N 30/46* (2006.01)

(52) U.S. Cl.
    CPC .............. *G01N 1/34* (2013.01); *G01N 30/02* (2013.01); *G01N 30/468* (2013.01); *Y10T 436/11* (2015.01); *Y10T 436/255* (2015.01)

(58) Field of Classification Search
    CPC ....................................................... G01N 1/34
    USPC ....................................................... 436/178
    See application file for complete search history.

(56) References Cited

U.S. PATENT DOCUMENTS

| 4,663,129 | A | * | 5/1987 | Atcher | G21G 4/08 250/432 PD |
| 5,378,895 | A | * | 1/1995 | Cole | G01T 1/167 250/370.03 |
| 7,261,812 | B1 | * | 8/2007 | Karp | B01D 15/1864 210/198.2 |

(Continued)

FOREIGN PATENT DOCUMENTS

GB 2024648 A * 1/1980 ............. B01D 59/30

OTHER PUBLICATIONS

Ronald E. Majors "Top 10 HPLC Column Myths" Jan. 1, 2007 LCGC Europe vol. 20, Issue 1.*

(Continued)

*Primary Examiner* — Christopher Adam Hixson
*Assistant Examiner* — Emily R. Berkeley
(74) *Attorney, Agent, or Firm* — Kevin E. West; Advent, LLP (57) ABSTRACT

A method includes supplying a reagent to a column, where the column is configured to purify an element from a sample matrix for isotopic analysis. The method also includes loading the column with the sample matrix, and supplying a second reagent to collect the element retained by the column. The method further includes loading the column with a second sample mixture, and collecting an element from the second sample mixture retained by the column. A column configured to separate an element from a sample matrix for isotopic analysis includes a resin configured to retain the element. The column also includes a first frit disposed of a first end of the column and a second frit disposed of a second end of the column. The column is configured to receive a first reagent in a first flow direction and a second reagent in a second flow direction different from the first flow direction.

8 Claims, 9 Drawing Sheets

(56) References Cited

U.S. PATENT DOCUMENTS

2004/0118189 A1* 6/2004 Karp .................. G01N 30/6095
 73/61.52
2012/0096932 A1* 4/2012 Anderson, Jr. ........ G01N 30/20
 73/61.53

OTHER PUBLICATIONS

David M. Fetterolf "Column Chromatography" Journal of Validation Technology [Spring 2009] pp. 43-48.*

* cited by examiner

PURIFYING AN ELEMENT FROM A SAMPLE MATRIX FOR ISOTOPIC ANALYSIS

CROSS-REFERENCE TO RELATED APPLICATIONS

The present application claims the benefit under 35 U.S.C. § 119(e) of U.S. Provisional Application Ser. No. 61/831,536, filed Jun. 5, 2013, and titled "COLLECTING MULTIPLE ANALYTES WITH THE SAME COLUMN," which is herein incorporated by reference in its entirety.

BACKGROUND

Liquid chromatography is a chromatographic technique used to separate a mixture of compounds for identifying, quantifying, and/or purifying individual components of the mixture.

SUMMARY

Systems and techniques for separating a first portion of a sample mixture from a second portion of the sample mixture are described. A method includes supplying a reagent to a column, where the column is configured to retain and purify an element from a sample matrix for isotopic analysis. The method also includes loading the column with the sample matrix, and supplying a second reagent to collect the element retained by the column. The method further includes loading the column with a second sample mixture, and collecting an element from the second sample mixture retained by the column. A column configured to separate an element from a sample matrix for isotopic analysis includes a resin configured to retain the element. The column also includes a first frit disposed of a first end of the column and a second frit disposed of a second end of the column. The column is configured to receive a reagent supplied to the column in either flow direction, allowing both forward and reverse loading and elution directions. In embodiments of the disclosure, a fully automated software controlled system is used to purify boron for isotopic analysis. The system can implement gas purge functionality (e.g., where air is inserted between reagents and/or a sample mixture and mobile phase), back elution functionality, and can be used to produce unfractionated samples. In some embodiments, flow rates, volumes, and so forth used in the system can be computer controlled.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

DETAILED DESCRIPTION

Liquid chromatography is a chromatographic technique used to separate a mixture of compounds for identifying, quantifying, and/or purifying individual components of the mixture. Chromatography can be described as a mass transfer process involving adsorption. A liquid and a sample mixture are passed through a column filled with a sorbent, leading to separation of the sample components. The active component of the column, the sorbent, is typically a granular material made of solid particles (e.g. silica, polymers, etc.). The components of the sample mixture are separated from each other due to their different degrees of interaction with the sorbent particles. High-performance liquid chromatography (HPLC) uses a pump to pass pressurized liquid and sample mixture through a column for separation of organic molecules and speciation. The liquid is typically a mixture of solvents and is referred to as "mobile phase."

Liquid chromatography for purification of single elements for isotopic analysis relies on the force of gravity to pass the mobile phase through the column. After using a column to separate a sample mixture, the column is discarded. Thus, when multiple sample mixtures are separated, multiple columns are prepared, used in parallel, and then discarded. Preparing each sample mixture and its associated column can be a time-consuming and labor-intensive process. Further, a new batch of sample mixtures and columns must be prepared in order to test another set of sample mixtures. Additionally, when relying on gravity to move the mobile phase through a column, liquid chromatography is a time-intensive process.

Accordingly, systems and techniques are described for processing multiple samples using the same column. Referring generally to FIGS. 1 through 5, a system is described. The system is configured to collect analytes for isotopic analysis (e.g., purifying elements such as boron for isotopic analysis). In accordance with the present disclosure, a column is provided that can be used with an automated system configured to supply the column with multiple reagents for separating multiple sample mixtures, one after another. In this manner, a single column is reused for the extraction of multiple samples. Sample mixtures, mobile phase, and reagents are supplied using one or more pumps, such as a syringe pump that are used to accurately and precisely control flow rates of, for example, reagents. As described, the systems and techniques disclosed herein can be used with a multi-collector inductively coupled plasma mass spectrometry (MC-ICP-MS) system. Further, techniques as described herein can be used with a multi-port valve to facilitate separation of multiple element specific fraction mixtures using different acid types. A column is disposed on the valve and configured to receive the multiple reagents. In embodiments of the disclosure, the column can be provided with sample mixtures, mobile phase, and/or reagents from different flow directions. For instance, flow through the column can be bidirectional.

Techniques of the present disclosure can be used to collect analytes including metals such as boron, lead, uranium, and so forth. Further, collection of the analytes can be used to perform an isotopic analysis. For example, an isotope ratio analysis can be conducted for elements such as lead, uranium, boron, strontium, and so forth. Additionally, by moving fluid through the system using a pump instead of a gravity drip, channeling is not necessarily created through the column. In embodiments of the disclosure, an example flow rate of a sample through the system can range from between at least approximately ten one-thousandths of a milliliter per minute (0.010 mL/min) to at least approximately ten milliliters per minute (10.000 mL/min). However, this range is provided by way of example only and is not meant to limit the present disclosure. In other embodiments, a sample flow rate of less than ten one-thousandths of a milliliter per minute (0.010 mL/min) or greater than ten milliliters per minute (10.000 mL/min) is used with the systems described herein. Using a pump instead of gravity reduces and/or eliminates vapor lock. Thus, it may not be necessary to continuously flow solution through the column in one direction. In some embodiments, flow rates, volumes, and so forth as used in the system are computer controlled.

In some embodiments, gas (e.g., air) is inserted between reagents and/or a sample mixture and mobile phase (e.g., to provide separation). The size of a gas bubble can be controlled to facilitate a desired flow of a sample mixture, a reagent, and so forth. For example, the size of a gas bubble can be varied based upon column backpressure.

In some embodiments, a column used in accordance with techniques of the present disclosure includes frits on both ends of the column (e.g., including a frit on an inlet end of the column and a frit on an outlet end of the column) that allow for bidirectional flow. Thus, as mobile phase and sample mixture is introduced to the column, the liquid passes into the column through, for example, a frit on an entry portion of the column. In embodiments of the disclosure, the column is formed of a material that can withstand the use of strong acids (e.g., an inert material, such as a fluoropolymer). Further, in some embodiments, some or all flow paths through the system (e.g., traversed by strong acids) are formed using inert material. For example, all fluoropolymer flow paths are used in the system.

Figure 7:
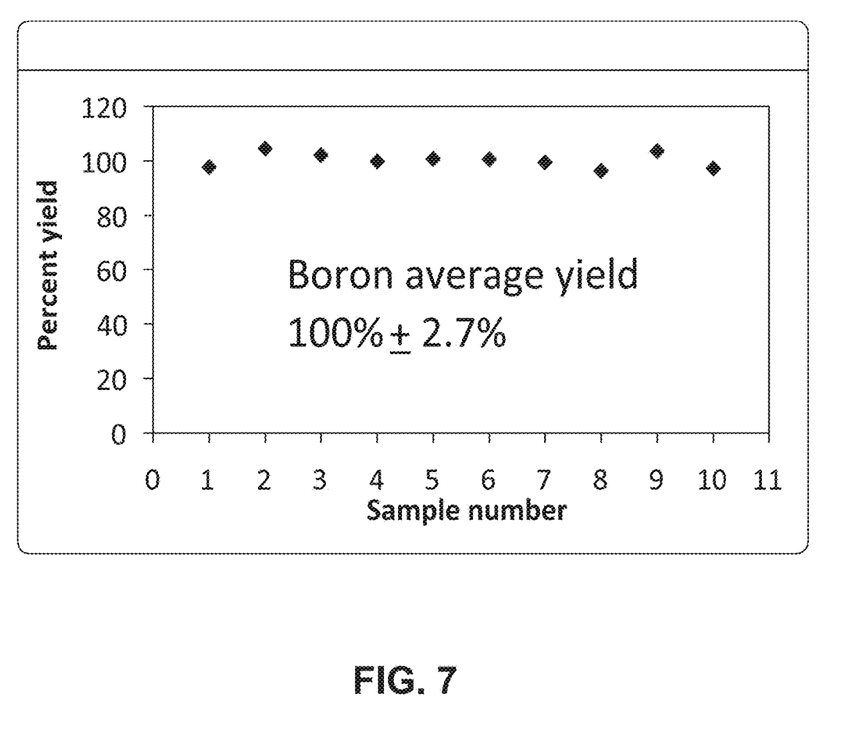
FIG. 7 is a graph illustrating data collected from twenty automated extractions of boron on one column alternating between a sample and a blank in accordance with an example embodiment of the present disclosure.
Figure 8:
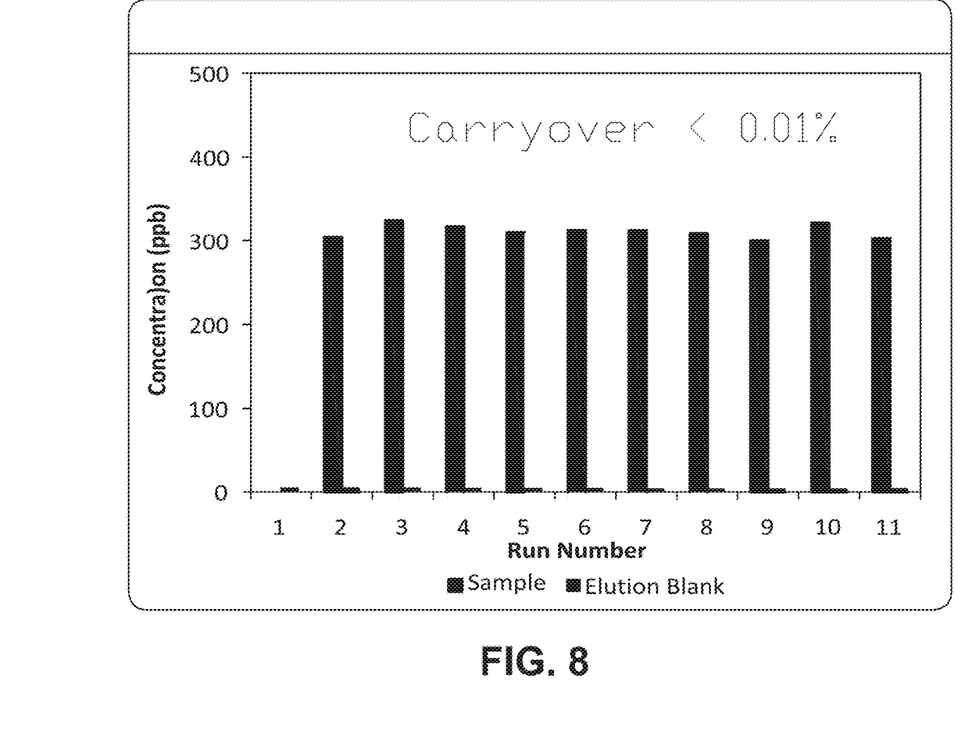
FIG. 8 is a graph illustrating an analysis of alternating blank and sample fractions, where boron values return to baseline concentrations for each blank in accordance with an example embodiment of the present disclosure.
Figure 9:
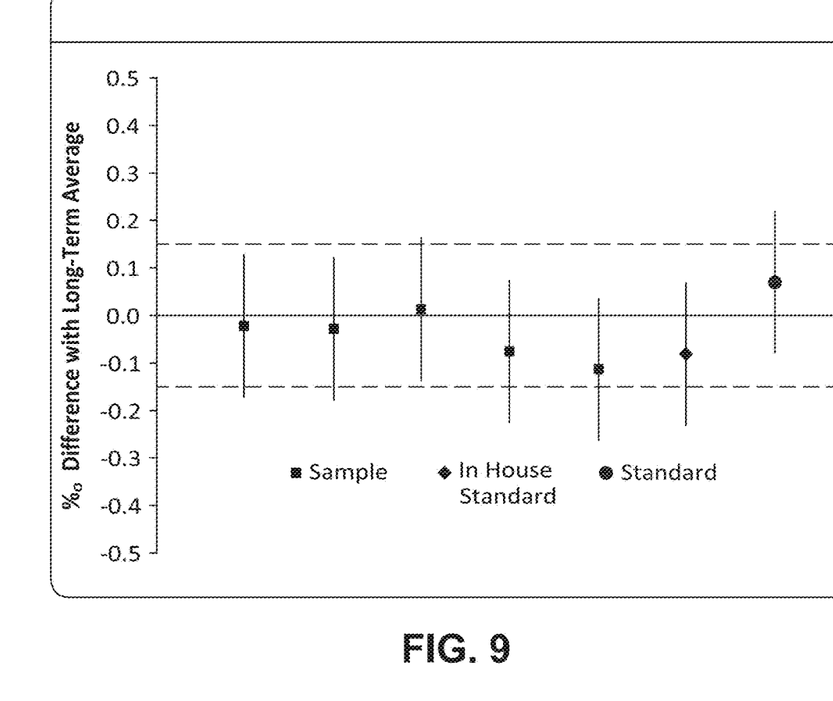
FIG. 9 is a graph illustrating a comparison of samples purified using a system configured to collect analytes for isotopic analysis in accordance with the present disclosure, such as the system illustrated in FIG. 1, to a long term average.
Figure 10:
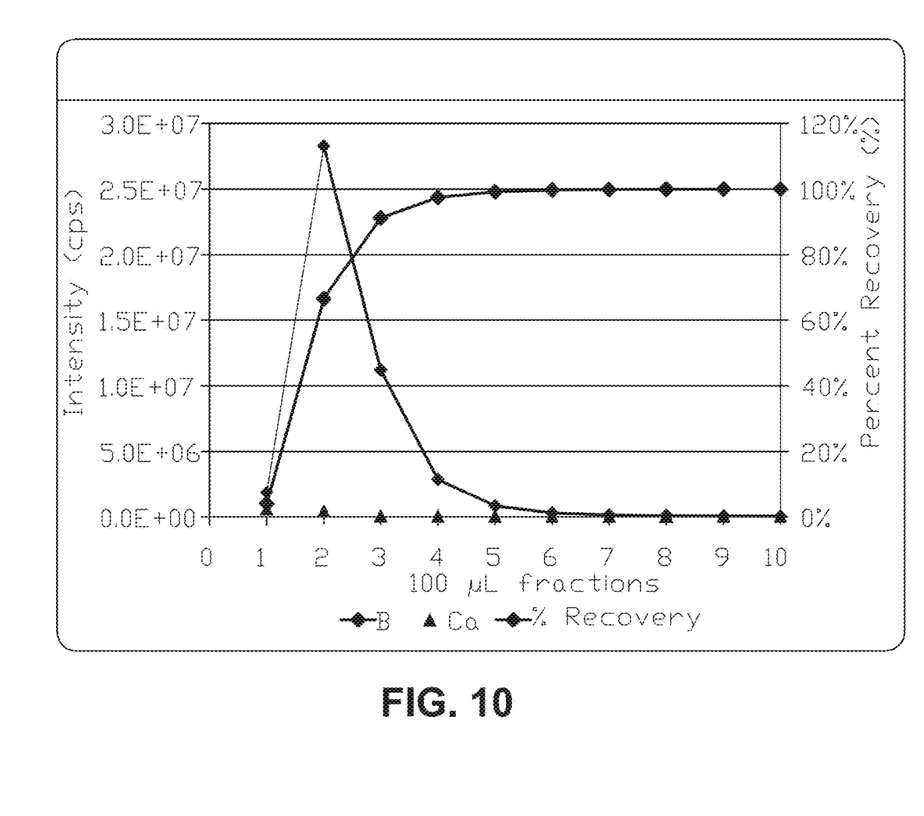
FIG. 10 is a graph illustrating ten one hundred microliter (100 μL) fractions collected using a system configured to collect analytes for isotopic analysis in accordance with the present disclosure, such as the system illustrated in FIG. 1, to generate an elution profile in accordance with example embodiments of the present disclosure.

Referring now to FIGS. 7 through 10, an example system is used to purify boron for isotopic analysis. With reference to FIG. 7, substantially complete elution of boron (e.g., greater than at least approximately ninety-nine and ninety-nine one-hundredths percent (99.99%) is achieved using multiple injections on one column. With reference to FIG. 8, substantially no carryover (e.g., less than at least approximately one one-hundredth of one percent (0.01%)) into a subsequent sample is achieved using multiple injections on one column with a three hundred microgram per liter (300 µg/L) sample. As shown in FIG. 8, when baseline boron concentration is subtracted from each blank, greater than at least approximately four (4) orders of magnitude washout is indicated. In this manner, boron contamination from the atmosphere can be eliminated (e.g., using inline chemistry). With reference to FIG. 9, small elution volumes with air segmentation are used to minimize or prevent boron fractionation that may otherwise invalidate the results of analysis. With reference to FIG. 10, reverse elution is used to prevent boron fractionation (e.g., in small volume samples). As shown in FIG. 10, baseline calcium and high recovery (e.g., ninety-nine and nine-tenths percent (99.9%) in six hundred microliters (600 µL)) indicate matrix removal and quantitative boron elution.

Figure 1:
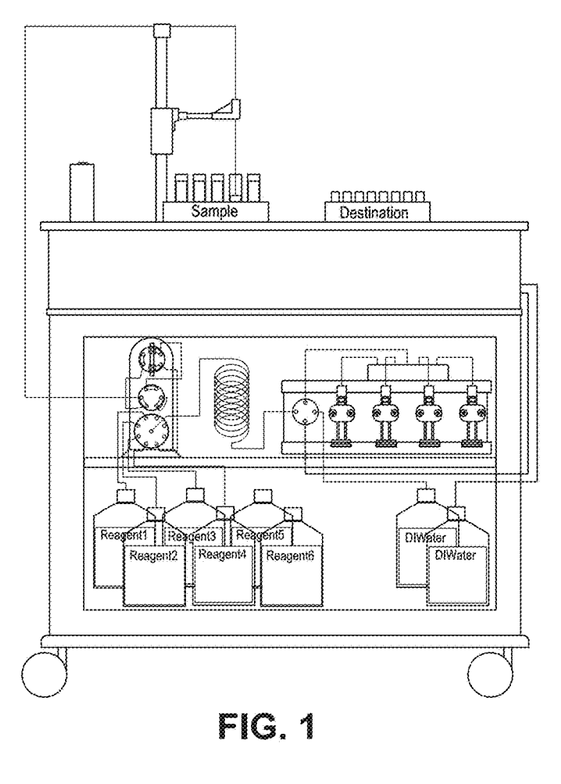
FIG. 1 is a diagrammatic illustration of a system configured to collect analytes for isotopic analysis in accordance with an example embodiment of the present disclosure.
Figure 2:
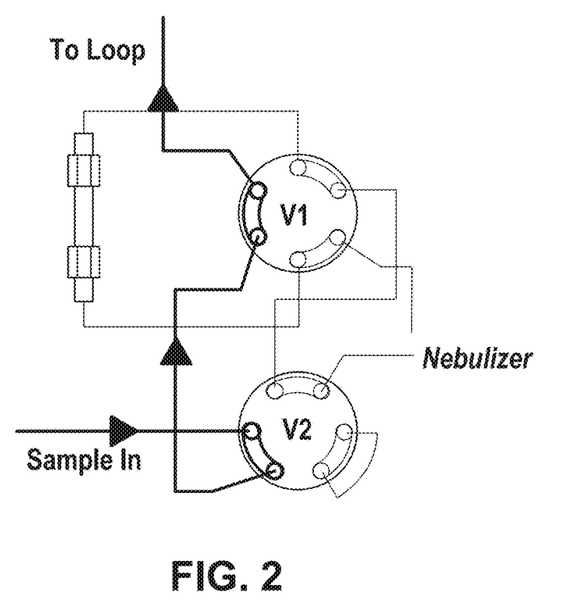
FIG. 2 is a partial schematic diagram of the system illustrated in FIG. 1, where a loop is loaded with a sample.
Figure 3:
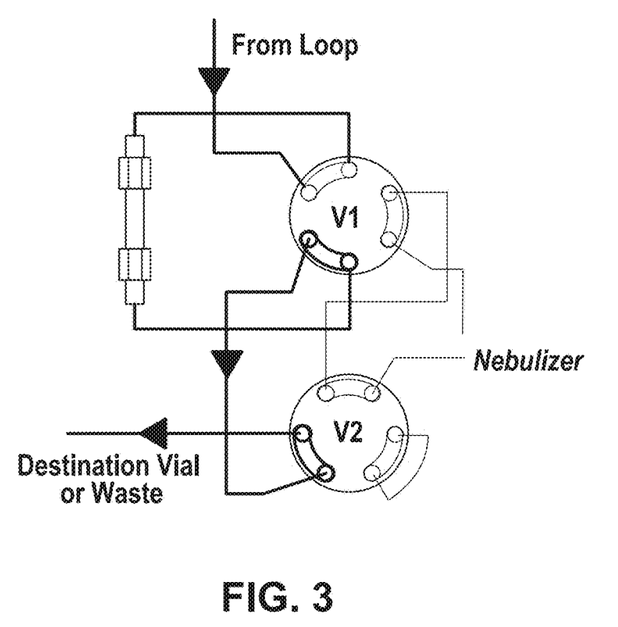
FIG. 3 is a partial schematic diagram of the system illustrated in FIG. 1, where the loop is dispensed onto a column and a sample or a reagent is pushed through the column to waste or a destination vial.
Figure 4:
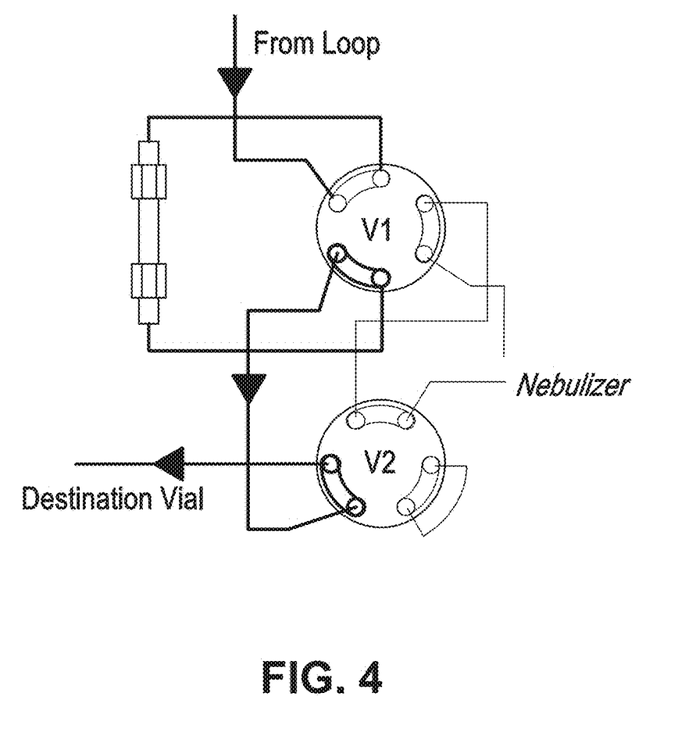
FIG. 4 is a partial schematic diagram of the system illustrated in FIG. 1, where the sample is eluted to a destination vial.
Figure 5:
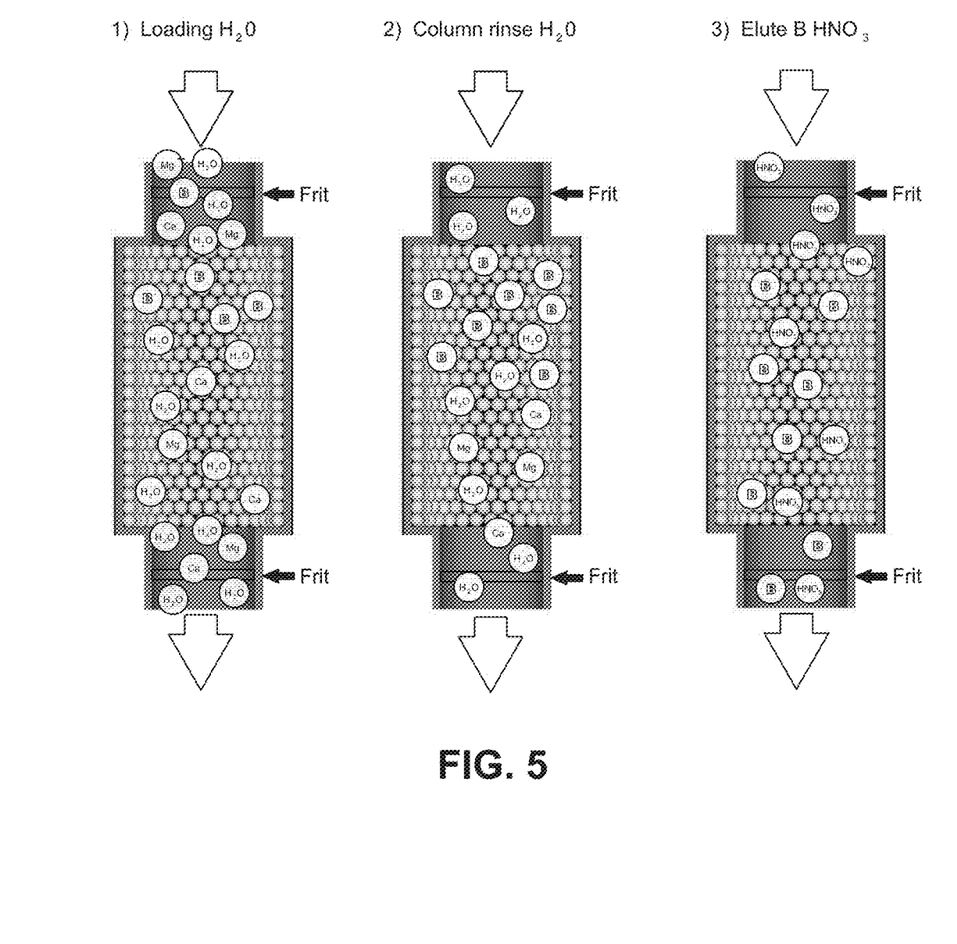
FIG. 5 is a diagrammatic illustration of chromatographic separation of boron from calcium, magnesium, and other matrix components.
Figure 6:
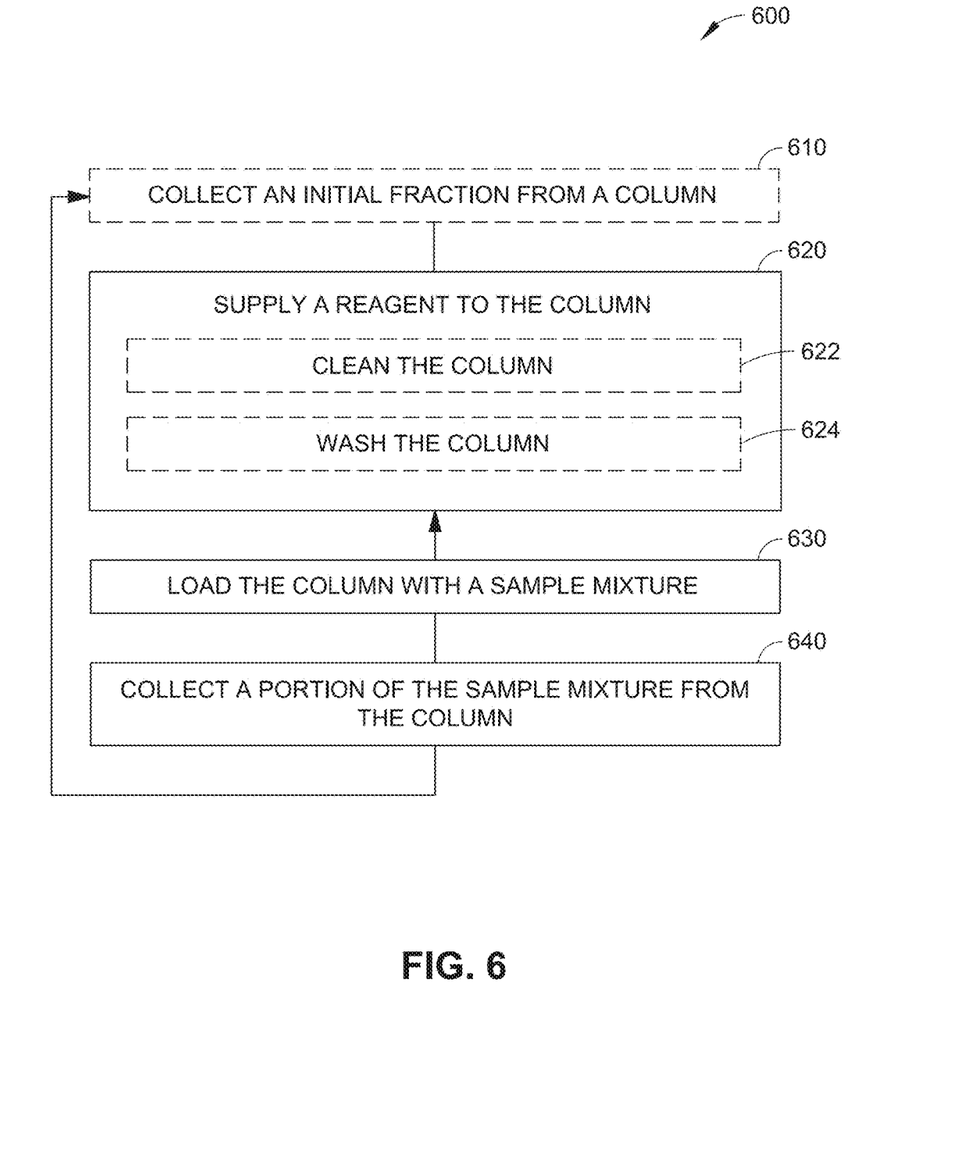
FIG. 6 is a flow diagram illustrating a method for separating a first portion of a sample mixture from a second portion of the sample mixture in accordance with example embodiments of the present disclosure.

FIG. 6 illustrates a procedure 600, in an example implementation, in which a single column is used to collect multiple analytes. In some embodiments, an initial fraction is collected from a column (Block 610). The initial fraction can be used to determine how clean the column is and/or whether there is any carryover from a previous sample. For example, when the column is used to separate boron from other components of a sample, a particular reagent can be selected to collect boron from the column. The reagent is supplied to the column, and the resulting fraction is analyzed to determine whether boron is present, how much boron is present, and so forth.

A reagent is supplied to the column (Block 620). In embodiments of the disclosure, the column has characteristics selected for separating a particular component (e.g., element) of a sample matrix. For example, the column uses a resin specific to an element of interest, such as boron. The chemistry in the column may also be specific to a particular molarity and/or strength of solution. For instance, a particular column may be specific to a ten percent (10%) nitric acid solution. Thus, a reagent having a specific molarity, pH, and so forth is selected for a column configured to retain boron atoms.

In some embodiments, the reagent is supplied to wash (e.g., clean) the column (Block 622). In some embodiments, the reagent is supplied to condition the column (Block 624). For example, a reagent is selected for a particular column configured to retain boron atoms as previously described. As described, multiple reagents are supplied to the column (e.g., one reagent for washing the column, another reagent for conditioning the column, a further reagent for further conditioning the column, and so forth). Additionally, reagents can be flushed and/or rinsed from a column. For example, a gas such as air can be used to push a reagent out of the column.

Next, the column is loaded with a sample mixture (Block 630). For instance, a sample matrix and mobile phase are supplied to the column. Then, the component of the sample mixture retained by the column is collected using, for example, a second reagent (Block 640). For example, the boron fraction can be eluted into a single vial by back flushing the column. In some embodiments, multiple reagents are used to collect multiple analytes. For example, one reagent can be used to collect thorium from the column, and a second reagent can be used to collect boron. Then, the process can be repeated. For example, the process 600 proceeds from Block 640 to Block 600 and/or Block 620. In this manner, the same column with the same resin is reused for multiple sample mixtures.

A system, including some or all of its components, can operate under computer control. For example, a processor can be included with or in a system to control the components and functions of systems described herein using software, firmware, hardware (e.g., fixed logic circuitry), manual processing, or a combination thereof. The terms "controller," "functionality," "service," and "logic" as used herein generally represent software, firmware, hardware, or a combination of software, firmware, or hardware in conjunction with controlling the systems. In the case of a software implementation, the module, functionality, or logic represents program code that performs specified tasks when executed on a processor (e.g., central processing unit (CPU) or CPUs). The program code can be stored in one or more computer-readable memory devices (e.g., internal memory and/or one or more tangible media), and so on. The structures, functions, approaches, and techniques described herein can be implemented on a variety of commercial computing platforms having a variety of processors.

The system can be coupled with and/or include a controller for controlling the collection of analytes for isotopic analysis. The controller can include a processor, a memory, and a communications interface. The processor provides processing functionality for the controller and can include any number of processors, micro-controllers, or other processing systems, and resident or external memory for storing data and other information accessed or generated by the controller. The processor can execute one or more software programs that implement techniques described herein. The processor is not limited by the materials from which it is formed or the processing mechanisms employed therein and, as such, can be implemented via semiconductor(s) and/or transistors (e.g., using electronic integrated circuit (IC) components), and so forth.

The memory is an example of tangible, computer-readable storage medium that provides storage functionality to store various data associated with operation of the controller, such as software programs and/or code segments, or other data to instruct the processor, and possibly other components of the controller, to perform the functionality described herein. Thus, the memory can store data, such as a program of instructions for operating the system (including its components), and so forth. It should be noted that while a single memory is described, a wide variety of types and combinations of memory (e.g., tangible, non-transitory memory) can be employed. The memory can be integral with the processor, can comprise stand-alone memory, or can be a combination of both.

The memory can include, but is not necessarily limited to: removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the system and/or the memory can include removable integrated circuit card (ICC) memory, such as memory provided by a subscriber identity module (SIM) card, a universal subscriber identity module (USIM) card, a universal integrated circuit card (UICC), and so on.

The communications interface is operatively configured to communicate with components of the system. For example, the communications interface can be configured to transmit data for storage in the system, retrieve data from storage in the system, and so forth. The communications interface is also communicatively coupled with the processor to facilitate data transfer between components of the system and the processor (e.g., for communicating inputs to the processor received from a device communicatively coupled with the controller). It should be noted that while the communications interface is described as a component of a controller, one or more components of the communications interface can be implemented as external components communicatively coupled to the system via a wired and/or wireless connection. The system can also comprise and/or connect to one or more input/output (I/O) devices (e.g., via the communications interface), including, but not necessarily limited to: a display, a mouse, a touchpad, a keyboard, and so on.

The communications interface and/or the processor can be configured to communicate with a variety of different networks, including, but not necessarily limited to: a wide-area cellular telephone network, such as a 3G cellular network, a 4G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to limit the present disclosure. Further, the communications interface can be configured to communicate with a single network or multiple networks across different access points.

Generally, any of the functions described herein can be implemented using hardware (e.g., fixed logic circuitry such as integrated circuits), software, firmware, manual processing, or a combination thereof. Thus, the blocks discussed in the above disclosure generally represent hardware (e.g., fixed logic circuitry such as integrated circuits), software, firmware, or a combination thereof. In the instance of a hardware configuration, the various blocks discussed in the above disclosure may be implemented as integrated circuits along with other functionality. Such integrated circuits may include all of the functions of a given block, system, or circuit, or a portion of the functions of the block, system, or circuit. Further, elements of the blocks, systems, or circuits may be implemented across multiple integrated circuits. Such integrated circuits may comprise various integrated circuits, including, but not necessarily limited to: a monolithic integrated circuit, a flip chip integrated circuit, a multichip module integrated circuit, and/or a mixed signal integrated circuit. In the instance of a software implementation, the various blocks discussed in the above disclosure represent executable instructions (e.g., program code) that perform specified tasks when executed on a processor. These executable instructions can be stored in one or more tangible computer readable media. In some such instances, the entire system, block, or circuit may be implemented using its software or firmware equivalent. In other instances, one part of a given system, block, or circuit may be implemented in software or firmware, while other parts are implemented in hardware.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A method for separating a first portion of a sample mixture from a second portion of the sample mixture, the method comprising:
   supplying a first reagent to a column, the column configured to purify at least a first element from a first sample matrix for isotopic analysis, the first element including boron;
   subsequent to supplying the first reagent to the column, loading the column with the first sample matrix;
   supplying a second reagent to collect the first element retained by the column, the second reagent including nitric acid;
   introducing a gas to the column to flush at least a portion of the column;
   collecting an initial fraction from the column subsequent to introducing the gas to the column to measure a carryover amount of boron present in the column;
   loading the column with a second sample mixture, the column having less than 0.01% carryover of boron prior to loading the column with the second sample mixture; and
   collecting a second element from the second sample mixture retained by the column.

2. The method as recited in claim 1, wherein the gas comprises air.

3. The method as recited in claim 1, wherein the column comprises a frit on an entry portion of the column.

4. The method as recited in claim 1, wherein a first direction of flow for one of the first sample matrix, the first reagent, or the second reagent into the column is different from a second direction of flow for another one of the first sample matrix, the first reagent, or the second reagent into the column.

5. The method as recited in claim 1, wherein supplying the first reagent to the column comprises washing the column.

6. The method as recited in claim 1, wherein supplying the first reagent to the column comprises conditioning the column.

7. The method as recited in claim 1, wherein the second element includes lead or uranium.

8. The method as recited in claim 1, wherein the column is formed of a fluoropolymer.

* * * * *